United States Patent
Hill

(12) 
(10) Patent No.: US 6,422,999 B1
(45) Date of Patent: Jul. 23, 2002

(54) METHOD OF MEASURING CONSUMER REACTION

(76) Inventor: Daniel A. Hill, 1268 Pennsylvania Ave., Apt. 2, San Diego, CA (US) 92103

( * ) Notice: Subject to any disclaimer, the term of this patent is extended or adjusted under 35 U.S.C. 154(b) by 0 days.

(21) Appl. No.: 09/568,263

(22) Filed: May 10, 2000

Related U.S. Application Data

(60) Provisional application No. 60/133,925, filed on May 13, 1999.

(51) Int. Cl.$^7$ .................................................. A61B 5/00
(52) U.S. Cl. ....................................................... 600/300
(58) Field of Search ............................... 600/300, 546, 600/558

(56) References Cited

U.S. PATENT DOCUMENTS

| | | | |
|---|---|---|---|
| 3,870,034 A | 3/1975 | James ...................... 128/2.1 Z |
| 4,448,203 A | 5/1984 | Williamson et al. ......... 128/733 |
| 4,794,533 A | 12/1988 | Cohen ................... 364/413.05 |
| 4,807,642 A | 2/1989 | Brown ........................ 128/733 |
| 4,817,628 A | 4/1989 | Zealear ....................... 128/741 |
| 4,859,050 A | * 8/1989 | Borah et al. ................. 351/210 |
| 4,964,411 A | 10/1990 | Johnson et al. ............. 128/733 |
| 5,092,343 A | 3/1992 | Spitzer et al. .............. 128/733 |
| 5,247,938 A | 9/1993 | Silverstein et al. .... 128/662.03 |
| 5,663,900 A | 9/1997 | Bhandari et al. ........... 364/578 |
| 5,676,138 A | 10/1997 | Zawilinski .................. 128/630 |
| 5,725,472 A | 3/1998 | Weathers ...................... 600/21 |
| 5,741,217 A | 4/1998 | Gero ........................... 600/547 |
| 5,772,591 A | 6/1998 | Cram ........................... 600/383 |
| 6,004,312 A | 12/1999 | Finneran et al. ............ 604/546 |
| 6,026,321 A | 2/2000 | Miyata et al. ............... 600/546 |
| 6,026,322 A | 2/2000 | Korenman et al. .......... 600/547 |

\* cited by examiner

*Primary Examiner*—Max Hindenburg
(74) *Attorney, Agent, or Firm*—Michael S. Sherrill

(57) ABSTRACT

A method of assessing consumer reaction to a marketing stimulus, involving the steps of (a) exposing a sample population to a marketing stimulus for an exposure period, (b) measuring surface electromyography signals from a zygomatic muscle of each member of the sample population during an exposure period, (c) optionally measuring surface electromyography signals from a corrugator facial muscle of each member of the sample population during the exposure period and combining the measured surface electromyography signals from the zygomatic and corrugator facial muscle of each member of the sample population to produce combined electromyography signals, (d) measuring electrodermography signals of each member of the sample population during the exposure period, (e) equating or translating the electromyography signals to an appeal value for each member, (f) equating or translating the electrodermography signals to an impact value for each member, and (g) visually representing each of the appeal and impact values identified by the marketing stimulus to which the members were exposed when the measurements were taken.

17 Claims, 3 Drawing Sheets

METHOD OF MEASURING CONSUMER REACTION

This application claims the benefit of provisional patent application Ser. No. 60/133,925 filed May 13, 1999.

FIELD OF THE INVENTION

The invention relates to methods of measuring consumer reaction to marketing stimuli.

BACKGROUND

Consumer reaction to a marketing stimulus (e.g., a television commercial) is typically assessed by means of exposing members of a focus group to the marketing stimulus (e.g., having the focus group watch the commercial) and obtaining the reactions and comments of the members immediately after exposure to the marketing stimulus by means of a written questionnaire and/or a personal interview. While generally effective, such a technique suffers from several drawbacks, including a tendency for members of a focus group to express inaccurately their reaction to marketing stimuli due to social pressure and limited self-awareness.

Hence, a longstanding need exists for a more reliable, scientific technique and methodology for measuring consumer reaction to marketing stimuli.

SUMMARY OF THE INVENTION

The invention is directed to a method of assessing consumer reaction to a marketing stimulus, involving the steps of (a) exposing a sample population of at least two members to a marketing stimulus for a period of time, (b) measuring surface electromyography signals from a zygomatic muscle of each member of the sample population during an exposure period, (c) optionally measuring surface electromyography signals from a corrugator facial muscle of each member of the sample population during the exposure period and combining the measured surface electromyography signals from the zygomatic and corrugator facial muscle of each member of the sample population to produce combined electromyography signals, (d) measuring electrodermography signals, selected from at least one of galvanic skin response signals, skin conductance level signals and skin potential level signals, of each member of the sample population during the exposure period, (e) equating or translating the electromyography signals to an appeal value for each member, (f) equating or translating the electrodermography signals to an impact value for each member, and (g) visually representing each of the appeal and impact values identified by the marketing stimulus to which the members were exposed when the measurements were taken.

By visually representing the appeal and impact values together for a given marketing stimulus for a given member (hereinafter "member set of appeal and impact values") on a single illustration, the overall relative marketing value of the stimulus (i.e., extent to which consumers were impacted and whether such impact was favorable or unfavorable) can be understood. When desired, the group appeal and impact values can be determined with the group appeal and group impact values visually represented on a single illustration.

The method preferably involves repeating steps (a) through (f) for several different marketing stimuli with members of the sample group, and then visually comparing sets of appeal and the impact values for each of the marketing stimuli so as to allow a relative comparison of the marketing stimuli.

DETAILED DESCRIPTION OF THE INVENTION INCLUDING A BEST MODE

Definitions

Figure 1:
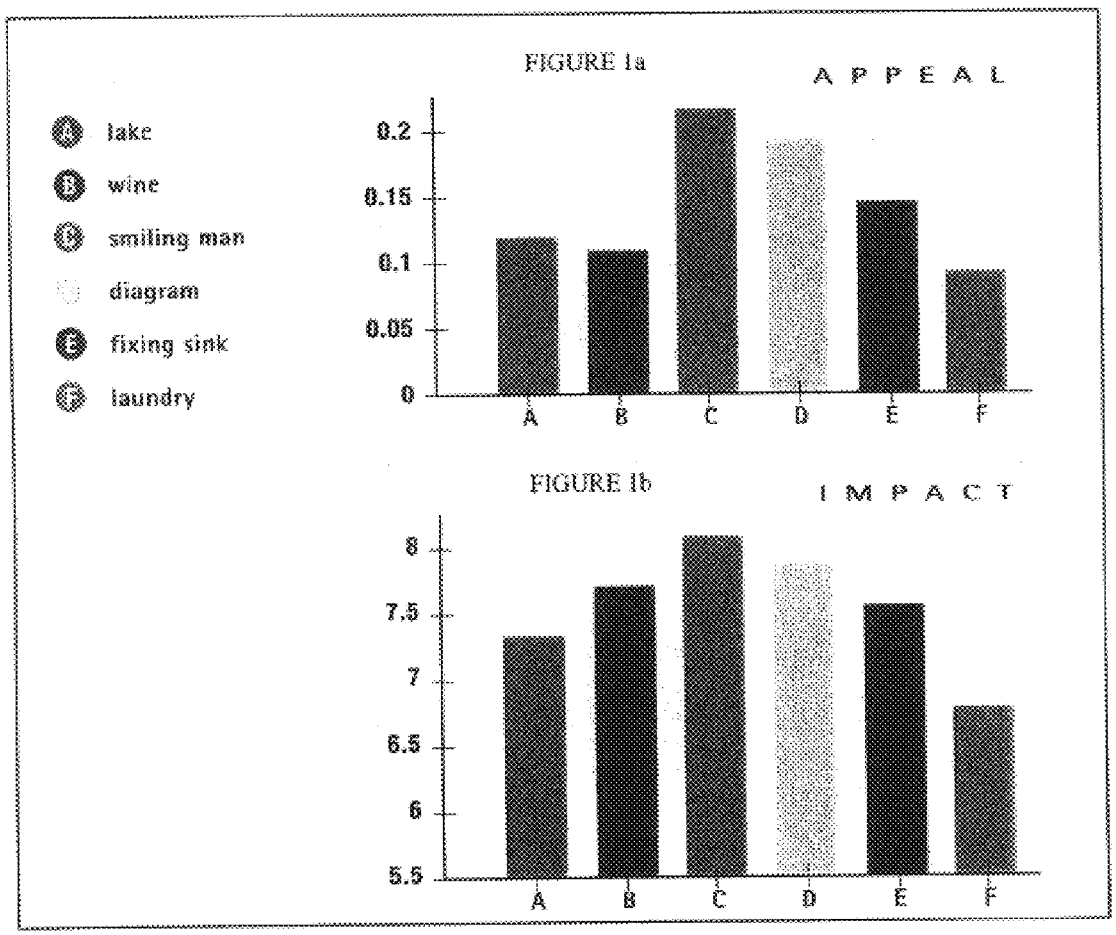
FIGS. 1a and 1b are bar graphs of the appeal and impact values for several stimuli obtained in Experiment One, set forth herein, and conducted in accordance with an embodiment of the invention.

As utilized herein, including the claims, the term "expose" means to submit or make accessible to one or more of the five senses of sight, hearing, taste, touch and smell.

As utilized herein, including the claims, the phrase "marketing stimulus" refers to an item selected and designed to (i) advertise, promote and/or enhance the sales or acceptance of a product and/or service, and/or (ii) advertise, promote, improve or enhance customer recognition and/or the public image of a person or business, and/or (iii) position a product, and/or (iv) enhance brand identity. Exemplary marketing stimuli include television commercials, radio advertisements, print advertisements, billboard advertisements, point-of-purchase displays, store-front signage, packaging, Yellow Pages advertisements, brochures, literature used in mass mailings, web sites, store layouts, interior design of a store, product appearance, product operation, presentation materials, etc.

As utilized herein, including the claims, the phrase "group appeal value" means a middle appeal value representative of a plurality of appeal values, selected from the various options for selecting or calculating a middle value including specifically, but not exclusively mean, median, and mode.

As utilized herein, including the claims, the phrase "group impact value" means a middle impact value representative of a plurality of impact values, selected from the various options for selecting or calculating a middle value including specifically, but not exclusively mean, median, and mode.

As utilized herein, including the claims, the term "average" means a middle value representative of a plurality of values, selected from the various options for selecting or calculating a middle value including specifically, but not exclusively mean, median, and mode.

As utilized herein, including the claims, the phrase "zygomatic muscle" includes zygomaticus major and zygomaticus minor.

As utilized herein, including the claims, the phrase "set of appeal and impact values" means the combination of an appeal value and an impact value obtained for a single member (hereinafter referenced as "member set of appeal and impact values") or the combination of an average appeal value and an average impact value obtained for a group of members (hereinafter referenced as "group set of appeal and impact values").

As utilized herein, including the claims, the term "illustration" includes graphs, charts and data tables.

As utilized herein, including the claims, the phrase "same media" means within a single type of medium, wherein types of media are separated as between (i) television, (ii) radio, (iii) print, (iv) internet, (v) three-dimensional architecture and interior design, (vi) fragrance, (vii) taste tests, (viii) use tests, and (ix) other.

As utilized herein, including the claims, the phrase "same type of goods or services" means goods or services which would be listed under the same topic heading in the most current US West Dex® Yellow Pages directory relative to the date of inquiry as to whether the goods or services are of the same type.

Method

A sample population must be chosen. The sample population may be chosen and prescreened according to any demographic, geographic or other marketing criteria of interest in accordance with the customary practice for selecting members of a focus group. The sample population must have at least two members, but may be as large as desired. Generally, a sample population of about 10 to 200 members, preferably 10 to 100 members, should provide statistically meaningful results at a reasonable cost. Sample populations having less than about 10 members tend to produce somewhat unreliable results, while sample populations of greater than about 200 significantly increase the cost of the study with only a modest improvement in reliability.

The members of the sample population are each attached ("wired") to an electrode or pair of electrodes for measuring electromyography activity (EMG) and an electrode for measuring electrodermal activity (EDA). Each member's skin is prepared in accordance with standard preparatory protocols for removing oils and lowering electrode impedance, applying an electrode cream, and then attaching the electrodes to the skin of the member. EMG signals and their relation to muscle functions are relatively well understood. Briefly, most muscles are controlled by nerves. Nerves cause the contraction of muscles by transmitting an electrical signal to the muscle. A voltage change occurs when a muscle contracts, creating an electric potential that is directly proportional to the strength of the contraction. EMG electrodes measure this voltage change from the external surface area of the individual. The EMG electrode is positioned over a zygomatic (i.e., smiling) muscle of the face. Optionally, additional EMG electrodes may also be positioned over one or more of (i) the zygomatic muscle on the other side of the face, (ii) a corrugator (i.e., frowning) facial muscle on the same side of the face as the zygomatic muscle being monitored, and/or (iii) a corrugator facial muscle on the opposite side of the face from the zygomatic muscle being monitored.

EDA signals and their relation to sweat gland activity are similarly relatively well understood. Sweat gland activity increases as the strength of an individual's reaction to a stimulus increases. Sweat gland activity produces sweat and changes pore size, which results in a proportional increase in the galvanic, electrical conductance and electrical potential of the skin. EDG electrodes measure this change in the skin. The EDG electrode may be positioned over any area of the body, with an industry preferences for the distal end of a finger.

The EMG and EDG electrodes are electrically connected to a suitable biofeedback system and central processing unit programmed to collect and report the EMG and EDG signals. Suitable biofeedback systems and central processing units for use in connection with EMG and EDG monitoring are available from a number of independent manufacturers. A suitable computerized biofeedback system is J&J Engineering model I-330 DSP.

The "wired" members are then exposed to a marketing stimulus for a period of time, during which EMG signals from a first zygomatic muscle of the wired member and EDG signals from the wired member are collected. Such EMG and EDG signals may be collected for selected portions or throughout the entire exposure period, with a preference for collecting such signals throughout the exposure period.

Optionally EMG signals are collected from (i) a second zygomatic muscle on the other side of the face, (ii) a first corrugator facial muscle on the same side of the face as the first zygomatic muscle, and/or (iii) a second corrugator facial muscle on the opposite side of the face from the first zygomatic muscle. Any such additional EMG signals may be combined with the EMG signals from the first zygomatic muscle to produce a combined EMG signal. Since the EMG signals represent the appeal of the marketing stimulus, with the zygomatic EMG signals representative of positive appeal and the corrugator EMG signals representative of negative appeal, the EMG signals may optimally be combined by adding or averaging the zygomatic EMG signals when EMG signals from more than one zygomatic muscle are collected, adding or averaging the corrugator EMG signals when EMG signals from more than one corrugator muscle are collected, and then reducing the value of the zygomatic EMG signals by the value of the corrugator EMG signal value. The values of the zygomatic EMG signals, corrugator EMG signals and/or combined EMG signals may be conditioned by any desired constant for purposes of shifting the final values as considered appropriate for facilitating understanding of the visually represented appeal and impact values.

A preferred mathematical algorithm for combining EMG signals from zygomatic muscles and EMG signals from corrugator muscles is provided below as Equations 1 and 2, wherein the combined EMG signal is a ratio of the difference between EMG signals from zygomatic muscles and EMG signals from corrugator muscles to the total EMG signals from the zygomatic and corrugator muscles. Equation 1 is used when unilateral (one-sided) EMG signals are measured for each of the zygomatic and corrugator muscles while Equation 2 is used when bilateral (two-sided) EMG signals are measured for each of the zygomatic and corrugator muscles.

$$\text{Combined } EMG = \frac{EMG\ Zygo - EMG\ Corr}{EMG\ Zygo + EMG\ Corr} \qquad \text{EQUATION 1}$$

$$\text{Combined } EMG = \frac{(EMG\ 1^{st}\ Zygo + EMG\ 2^{nd}\ Zygo) - (EMG\ 1^{st}\ Corr + EMG\ 2^{nd}\ Corr)}{(EMG\ 1^{st}\ Zygo + EMG\ 2^{nd}\ Zygo) + (EMG\ 1^{st}\ Corr + EMG\ 2^{nd}\ Corr)} \qquad \text{EQUATION 2}$$

The period of time for which members of the sample population are exposed to the marketing stimulus can vary considerably depending upon a number of variables, including the type of goods and/or services involved, the type of media and the normal duration of exposure in the real world. Generally, an exposure period of between about 5 to 30 seconds is sufficient. Of course, longer exposure periods are possible in those instances where a longer exposure period is necessary to imitate accurately actual consumer experience, such as when viewing the interior design of a shopping mall or a video. Exposure periods of less than about five (5) seconds do not always provide sufficient time for the members to view completely and physiologically react to the marketing stimulus.

The EMG and EDG signals can be collected at any desired frequency from thousands of times a second to once every several seconds depending upon the desired information and time sensitivity of the marketing stimulus (e.g., collection is required at a high frequency when one of the goals of the testing is to determine how long to display each given scene in a television commercial).

The EMG and EDG signals can be collected throughout the exposure period and a period of time before and after the exposure period for purposes of establishing a base-line and post stimulation level for the member. Establishing a base-line and post simulation level for each member allows detailed analysis of the EMG and EDG signals, such as allowing the appeal and impact values to be visually represented in the form of a change in appeal and impact values resulting from exposure to the marketing stimulus as well as the absolute value of the appeal and impact values.

The EMG signals, single or combined, are equated (i.e., direct transfer) or translated (i.e., amplified, compressed, converted to a ratio, etc.) to an appeal value. Similarly, the EDG signals are equated or translated to an impact value.

The appeal value and impact value can then be visually represented along with an identification of the marketing stimulus to which the members were exposed when the EMG and EDG signals were measured. The values may be representative of a single member of the sample population, the group value of a defined subset of the sample population (e.g., single males 20 to 30 years old, persons with an average household income of less than $40,000 per year, etc.), or the group value of the entire sample population. Standard rules of statistical analysis may be employed to the extent necessary and appropriate when group averages are represented.

The appeal and impact values may be visually represented in any desired manner, including specifically but not exclusively, in the form of a table, chart or graph (hereinafter collectively referenced as an "illustration"). The appeal and impact values may be represented on the same or separate illustrations.

The members of the sample population may be sequentially exposed to different marketing stimuli, preferably within the same media and for the same type of goods or services, for purposes of allowing a comparison of the set of appeal and the impact values for each of the marketing stimuli. When members are sequentially exposed to different marketing stimuli, they should be given "down" time of at least several seconds between exposures to the marketing stimuli, during which time the member is not subjected to any stimuli, for purposes of allowing the member to return to a base-line level of arousal.

EXAMPLES

Example One (Plumbers)

A sample population of 10 members recruited at random from plumbing supply stores or general hardware stores were connected to a biofeedback unit, model I-330 DSP purchased from J&J Engineering, with EMG electrodes placed over a zygomatic muscle and a corrugator muscle on the same side of the face, and an EDG electrode placed over the distal end of the left index finger.

After a proper initial conditioning period of several seconds during which the members were not knowingly exposed to any new stimuli, the biofeedback unit was activated to begin the collection of EMG and EDG signals every second. Upon establishing an initial base line for the member, the member was sequentially exposed for 6 seconds each to a lake scene (A), a wine bottle (B), a smiling man (C), a diagram containing factual data (D), a person fixing a sink (E) and a basket of laundry (F), with several seconds of down time between each stimulus during which the member was asked to stare at a blank white sheet of paper. The value of the zygomatic EMG signals, corrugator EMG signals and EDG signals for each member were collected every second during the exposure periods and the average value used in the following equations to establish a group appeal value and a group impact value for each of the stimuli.

$Appeal_{Member} = (Zygo_{avg} - Corr_{avg})/(Zygo_{avg} + Corr_{avg})/$
$Impact_{Member} = EDG_{avg}$
$Appeal_{group} = \Sigma\ Appeal_{Members}/\#\ of\ Members$
$Impact_{Group} = \Sigma\ Impact_{Members}/\#\ of\ Members$ The group appeal and group impact values are visually represented in separate bar graphs in FIGS. 1a and 1b.

Example Two (Kids)

A sample population of 20 members recruited at random from three communities nationwide were connected to a biofeedback unit, model I-330 DSP purchased from J&J Engineering, with EMG electrodes placed over a zygomatic muscle and a corrugator muscle on the same side of the face, and an EDG electrode placed over the distal end of the left index finger.

After a proper conditioning period of several seconds during which the members were not knowingly exposed to any new stimuli, the biofeedback unit was activated to begin the collection of EMG and EDG signals every second. Upon establishing an initial base line for the member, the member was sequentially exposed for exactly 6 seconds each to prints of a red fox (1), a leaping fox (2), a preview fox (3), a glasses fox (4), a first fabric (5), a second fabric (6), a third fabric (7), a fourth fabric (8), and prototype of a first box (9), a second box (10), a third box (11) and a fourth box (12), with several seconds of down time between each stimulus during which the member was asked to stare at a blank white sheet of paper. The value of the zygomatic EMG signals, corrugator EMG signals and EDG signals for each member were collected every second during the exposure periods and the average value used in the following equations to establish a group appeal value and a group impact value for each of the stimuli.

Figure 2:
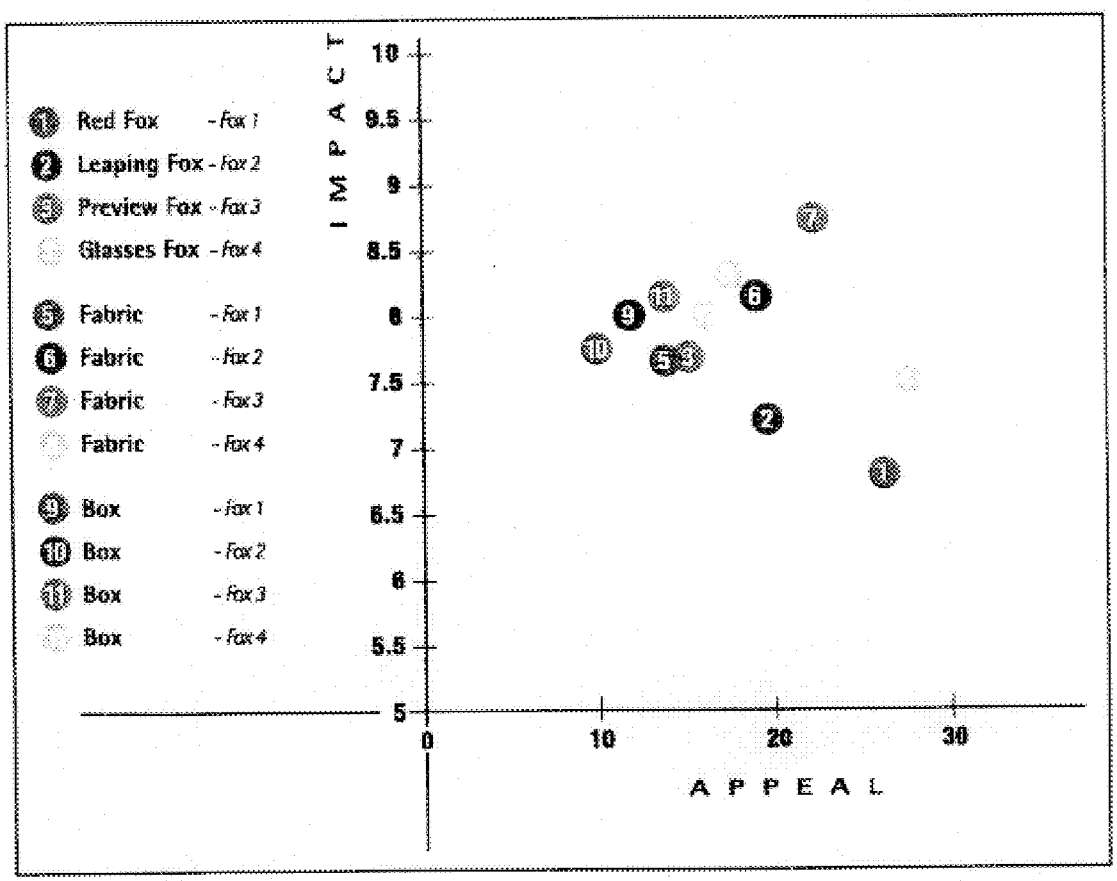
FIG. 2 is a coordinate graph plotting appeal versus impact values for several stimuli obtained in Experiment Two, set forth herein, and conducted in accordance with an embodiment of the invention.

$Appeal_{Member} = (Zygo_{avg} - Corr_{avg})/(Zygo_{avg} + Corr_{avg})/$
$Impact_{Member} = EDG_{avg}$
$Appeal_{Group} = \Sigma\ Appeal_{Members}/\#\ of\ Members$
$Impact_{Group} = \Sigma\ Impact_{Members}/\#\ of\ Members$ The group appeal and group impact values are visually represented by a dot on the coordinate graph in FIG. 2.

Example Three (Hotels)

A sample population of 40 members recruited at random from among business leisure travelers were connected to a biofeedback unit, model I-330 DSP purchased from J&J Engineering, with EMG electrodes placed over a zygomatic muscle and a corrugator muscle on the same side of the face, and an EDG electrode placed over the distal end of the left index finger.

After a proper conditioning period of several seconds during which the members were not knowingly exposed to any new stimuli, the biofeedback unit was activated to begin the collection of EMG and EDG signals every second. Upon establishing an initial base line for the member, the member was sequentially exposed to four 15 to 30 second television commercials for four separate national hotel chains, with several seconds of down time between each stimulus during which the member was asked to stare at a blank screen. The value of the zygomatic EMG signals, corrugator EMG signals and EDG signals for each member were collected every second during the exposure periods and the average value used in the following equations to establish a group appeal value and a group impact value for each of the stimuli.

Figure 3:
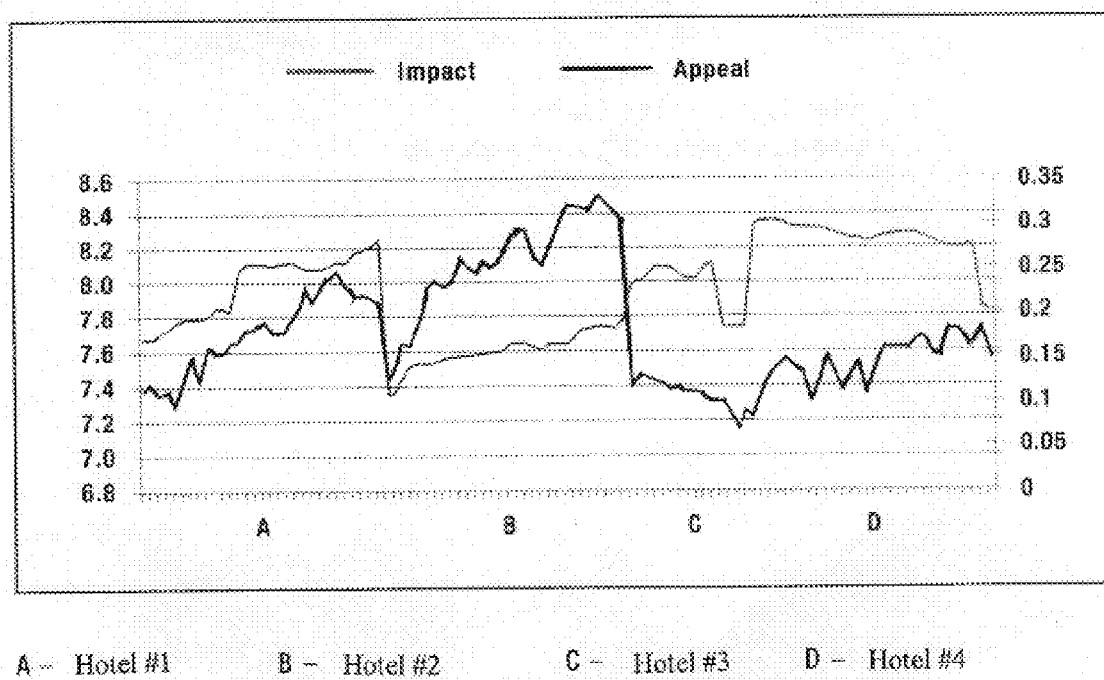
FIG. 3 is a coordinate graph plotting appeal and impact values versus time for several stimuli obtained in Experiment Three, set forth herein, and conducted in accordance with an embodiment of the invention.

$Appeal_{Member} = (Zygo_{avg} - Corr_{avg})/(Zygo_{avg} + Corr_{avg})/$
$Impact_{Member} = EDG_{avg}$ $Appeal_{Group} = \Sigma\ Appeal_{Members}/\#\ of\ Members$ $Impact_{Group} = \Sigma\ Impact_{Members}/\#\ of\ Members$ The group appeal and group impact values are visually represented over time on the coordinate graph in FIG. 3.

I claim:

1. A method of assessing consumer reaction to a marketing stimulus, comprising:
   (a) exposing a sample population comprised of a plurality of members to a marketing stimulus for a period of time;
   (b) measuring surface electromyography signals from a zygomatic muscle of each member of the sample population during an exposure period;
   (c) measuring electrodermography signals, selected from at least one of galvanic skin response signals, skin conductance level signals and skin potential level signals of each member of the sample population during an exposure period;
   (d) equating or translating the electromyography signals to an appeal value for each member;
   (e) equating or translating the electrodermography signals to an impact value for each member; and
   (f) visually representing each of the appeal and impact values identified with the marketing stimulus to which the members were exposed when the measurements were taken.

2. The method of claim 1 further comprising: (g) measuring surface electromyography signals from a corrugator facial muscle of each member of the sample population during an exposure period, and (h) combining the measured surface electromyography signals from the zygomatic and corrugator facial muscle of each member of the sample population to produce a combined electromyography signal, wherein the combined electromyography signal is the electromyography signal equated or translated to the appeal value for each member.

3. The method of claim 1 further comprising (j) visually representing at least one set of appeal and impact values of at least one member together on a single illustration.

4. The method of claim 1 further comprising: (k) repeating steps (a) through (e) with members of the sample population for at least one other marketing stimulus which is different from the first marketing stimulus, and (m) visually comparing the set of appeal and impact values of each marketing stimulus.

5. The method of claim 4 wherein the marketing stimuli are within the same media.

6. The method of claim 4 wherein the marketing stimuli market the same type of goods or services.

7. The method of claim 1 wherein the sample population is comprised of between about 10 to 200 members.

8. The method of claim 4 wherein the sample population is comprised of between about 10 to 100 members.

9. The method of claim 1 wherein the surface electromyography signals and electrodermal signals are measured throughout the exposure period, a period of time before the exposure period and a period of time after the exposure period.

10. The method of claim 4 wherein (i) a period of time is provided between sequential exposures to marketing stimuli during which the members are not exposed to any marketing stimuli and (ii) the surface electromyography signals and electrodermal signals are measured throughout each exposure period and for a period of time before and after each exposure period.

11. The method of claim 1 wherein the combined surface electromyography signal is calculated by dividing the difference between the zygomatic and corrugator facial muscle signals by the sum of the zygomatic and corrugator facial muscle signals.

12. The method of claim 2 further comprising (j) visually representing at least one set of appeal and impact values of at least two members together on a single illustration.

13. The method of claim 1 wherein a group set of appeal and impact values is visually represented.

14. The method of claim 13 wherein the visually represented group set of appeal and impact values is an average appeal value and an average impact value for the sample population.

15. The method of claim 1 wherein electromyography signals are separately measured for bilateral zygomatic muscles of each member of the sample population during an exposure period and the measured surface electromyography signals for the bilateral zygomatic muscles of each member of the sample population is combined to produce a combined electromyography signal, wherein the combined electromyography signal is the electromyography signal equated or translated to the appeal value for each member.

16. The method of claim 2 wherein electromyography signals are separately measured for bilateral zygomatic and corrugator facial muscles.

17. The method of claim 2 wherein electromyography signals are separately measured for zygomatic and corrugator facial muscles on the same side.

* * * * *